United States Patent [19]

Semonsky et al.

[11] 4,064,130
[45] Dec. 20, 1977

[54] Nβ-SUBSTITUTED 8-β-AMINOETHYLERGOLIN-I DERIVATIVES AND THEIR MANUFACTURE

[75] Inventors: Miroslav Semonsky; Antonin Cerny; Marie Krajcrova; Karel Rezabeck; Marie Auskova; Miroslav Seda, all of Prague; Bohumil Sevcik; Josef Kral, both of Pohori-Chotoun, all of Czechoslovakia

[73] Assignee: SPOFA, Pharmaceutical Works, Prague, Czechoslovakia

[21] Appl. No.: 597,389

[22] Filed: July 18, 1975

[30] Foreign Application Priority Data

July 19, 1974 Czechoslovakia ............... 5178/74

[51] Int. Cl.$^2$ ............................................ C07D 457/02
[52] U.S. Cl. ............................... 260/285.5; 424/261
[58] Field of Search ....................................... 260/285.5

[56] References Cited

U.S. PATENT DOCUMENTS

| 3,228,942 | 1/1966 | Camerino et al. | 260/285.5 |
| 3,557,118 | 1/1971 | Arcamone et al. | 260/285.5 |
| 3,646,046 | 2/1972 | Arcamone et al. | 260/285.5 |
| 3,972,883 | 8/1976 | Areari et al. | 260/285.5 |
| 3,996,228 | 12/1976 | Arcari et al. | 260/285.5 |
| 4,005,090 | 1/1977 | Semonsky et al. | 260/285.5 |

FOREIGN PATENT DOCUMENTS

| 523,781 | 4/1956 | Canada | 260/285.5 |
| 1,230,260 | 4/1971 | United Kingdom | 260/285.5 |

OTHER PUBLICATIONS

Bernaidi et al.; Gazz. Chem. et al., vol. 94, pp. 969–978, (1964).

Primary Examiner—Donald G. Daus
Assistant Examiner—Mary C. Vaughn

[57] ABSTRACT

Novel Nβ-substituted 8-β-aminoethylergolin-I derivatives and the acid addition salts thereof are disclosed. The described compositions are prepared by either reductive alkylation or selective reduction of corresponding derivatives containing carbonyl groups.

1 Claim, No Drawings

Nβ-SUBSTITUTED 8-β-AMINOETHYLERGOLIN-I DERIVATIVES AND THEIR MANUFACTURE

This invention relates to a method for the preparation of Nβ-substituted derivatives of 8-β-aminoethylergolin-I and the compositions so produced. More particularly, the present invention relates to a method for the preparation of Nβ-substituted derivatives of 8-β-aminoethylergolin-I and pharmaceutically active addition salts thereof by a chemical reduction process.

The Nβ-substituted derivatives of 8-β-aminoethylergolin-I described herein are of the general formula (1)

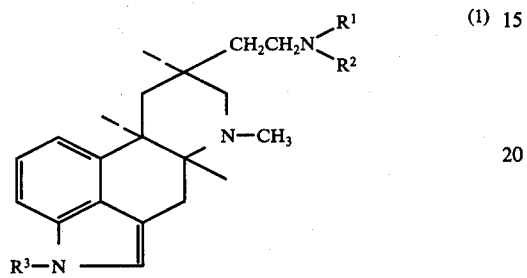

Wherein $R^1$ is selected from the group consisting of (a) alkyl groups having from 1-8 carbon atoms, (b) a phenylalkyl group of the general formula

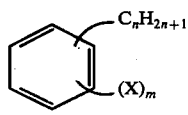

wherein
$n$ is an integer from 1-4, and X is selected from the group consisting of chlorine, bromine, a hydroxyl group and an alkoxy group having from 1-4 carbon atoms, $m$ being an integer from 1-3,
wherein $R^2$ is selected from the group consisting of hydrogen and an alkyl group having from 1-4 carbon atoms, and $R^3$ is selected from the group consisting of hydrogen and a methyl group.

The desired compositions upon acidification with either organic or inorganic acids have been found to yield addition salts which evidence pharmacological activity suitable for use in human and veterinary therapy. Studies have revealed that these compositions inhibit prolactin secretion in the adenohypophysis and stimulate the secretion of gonadotropins therein. The prolactin inhibitory effect of such compositions manifests itself by antinidation and anti-lactation effects, by the noted stimulation of secretion and by inducing oestrus. From the pathophysiological standpoint, the compounds described herein may be utilized in those cases wherein it is considered advantageous to lower the prolactin level or to elevate the level of gonadotropins in the blood system of humans and animals. Studies have also revealed that the novel compounds herein are of negligible toxicity and tend to reduce the weight of the prostate in the course of animal experimentation.

Alkyl groups suitable for substitution as $R^1$ in the generic formulation alluded to hereinabove include methyl, ethyl, n-propyl, isopropyl, n-butyl, isobutyl, secondary butyl, tertiary butyl, n-pentyl, isopentyl, 2-pentyl, 3-pentyl, n-hexyl, n-octyl, etc. groups. $R^1$ phenylalkyl groups found to be particularly suited for use in the practice of the present invention are benzyl, 4-hydroxybenzyl, 4-methoxybenzyl, 1-phenyl-1-ethyl, 1-(p-methoxyphenyl)-1-ethyl, etc.

In accordance with the present invention, Nβ-substituted 8-β-aminoethylergolin-I of the general formula (1), set forth above, may conveniently be prepared by:

A. reaction of β-aminoethylergolin-I of the general formula (2),

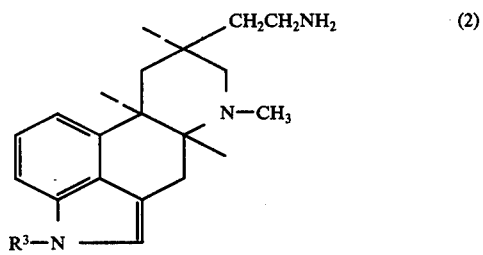

wherein $R^3$ is as represented in formula (1), with an aldehyde or ketone of the general formula (3), $R^4$—CO—$R^2$, wherein $R^2$ is as represented in formula (1) and $R^4$ is selected from the group consisting of hydrogen, an alkyl group having the formula $C_pH_{2p+1}$ wherein $p$ is an integer from 1-7, and a phenyl group having the formula

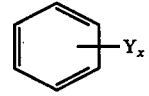

wherein Y is selected from the group consisting of chlorine, bromine, hydroxyl and an alkoxy group having from 1-4 carbon atoms and $x$ is an integer from 1-3, the resultant intermediate being hydrogenated, without isolation, with hydrogen in the presence of a catalyst;

B. reduction of substituted 6-methyl-8-ergolinyl-I acetamides of the general formula (4),

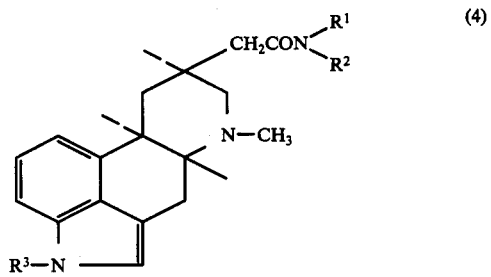

wherein $R^1$, $R^2$ and $R^3$ are as defined in formula (1), with a reagent capable of selectively reducing the carbonyl group, as for example, a complex metal hydride; or C. reduction of β-acylaminoethylergolin-I of the general formula (5)

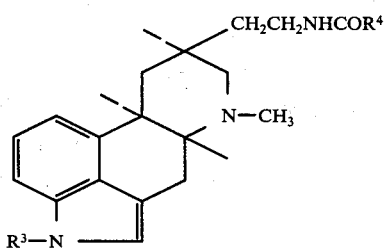

wherein $R^3$ and $R^4$ are as previously defined, with a reagent capable of selectively reducing the carbonyl group, as for example, a complex metal hydride.

The reductive alkylation reaction, designated (A), may conveniently be effected by the hydrogenation of a mixture comprising the β-aminoethylergolin-I of formula (2) with 1-3 molecular equivalents of the aldehyde or ketone of formula (3) in a suitable solvent in the presence of a catalyst. The hydrogenation reaction is conducted at hydrogen pressures ranging from 1-70 atmospheres at temperatures within the range of 10°-140° C, a general preference existing at temperatures within the range of 20°-50° C. Hydrogenation catalysts suitable for this purpose include palladium, platinum or Raney nickel and such catalysts may be employed upon conventional supports. The solvents chosen for such reaction may be alcohols such as methanol, ethanol, propanol, 2-propanol, and the like, ethers such as tetrahydrofuran or dioxane, and mixtures of the forgoing solvents with water.

Although the aldehydes or ketones are employed herein in molecular equivalents ranging from 1-3 per molecular equivalent of amino compound, a preference is found to exist for the use of a slight molar excess of aldehyde or ketone ranging from 1.1-1.5 molar equivalents per 1 molar equivalent of amino compound.

Aldehydes and ketones found to be of particular use for this purpose are formaldehyde, acetaldehyde, propionaldehyde, butyraldehyde, isobutyraldehyde, valeraldehyde, n-hexanal, n-heptanal, n-octanal, benzaldehyde, p-methoxybenzaldehyde, acetone, methyl ethyl ketone, methyl propyl ketone, diethyl ketone, acetophenone and p-methoxyacetophenone.

In the operation of the described reductive alkylation process, the reaction mixture is initially filtered to remove the catalyst, the solvent is evaporated and the desired aminoethylergolin-I derivative isolated either by crystallization and/or column chromatography. Alternatively, the crude amino derivative may be transformed into a corresponding addition salt by reaction with an organic or inorganic acid and, subsequently, purified in the form of a salt.

The β-aminoethylergolin-I of general formulation (2) which is employed as the starting component in the foregoing reductive alkylation process is described in copending application, Ser. No. 560,106, filed Mar. 19, 1975, now U.S. Pat. No. 4,005,090.

The preparation of the novel Nβ-substituted derivatives of 8-β-aminoethylergolin-I of formula (1) may, alternatively, be prepared pursuant to methods (B) and (C) by the reduction of carbonyl compounds of general formulae (4) and (5) by means of complex metal hydrides. Hydrides found to be particularly useful for this purpose are sodium borohydride, sodium bis-(2-methoxyethoxy) aluminum hydride, and the like. Diborane is also useful for this purpose. The carbonyl compound reductions are conducted in an inert solvent, preferably in an ether such as tetrahydrofuran, dioxane, diethyl ether and the like, at temperatures ranging from 0-80° C preferably utilizing a 1-5 molar excess of reducing agent. The resultant product may be isolated by conventional techniques, as for example, by decomposition of the resultant complex by adding water thereto with subsequent extraction of the product in an inert, water immiscible solvent such as chloroform, dichloromethane, ether or mixtures thereof with alcohols such as methanol and ethanol.

Substituted amides of the type shown in general formulation (4) suitable for use in the synthesis identified in (B) above are described in British patent specification No. 1,264,779 whereas compounds of formula (5) required for synthesis (C) above are described in said copending application, Ser. No. 560,106, filed Mar. 19, 1975, now U.S. Pat. No. 4,005,090.

The pharmaceutically active addition salts referred to above are prepared by reacting 1 molar equivalent of formula (1) with from 1-3 molecular equivalents of an organic or inorganic acid in a solvent, typically methanol, ethanol, water or mixtures thereof. Acids found to be particularly suitable for this purpose are sulfuric, hydrochloric, hydrobromic, methanesulfonic, tartaric, maleic and the like. Bis hydrogen maleates prepared in the foregoing manner are found to crystallize readily from alcohols and are soluble in water, so suggesting their use in oral and enteral applications.

Several examples of the present invention are set forth in detail below. It will be understood that these exemplary embodiments are for purposes of exposition only and are not to be construed as limiting.

EXAMPLE 1

D-6-methyl-8-β-isopropylaminoethylergolin-I 0.32 gram of acetone (5.5 mmol) and 75 mg. of Adams catalyst were added to a solution comprising 1.35 grams (5 mmol) of D-6-methyl-8-β-aminoethylergolin-I in 75 ml. of ethanol and the resultant mixture hydrogenated with shaking at a temperature of 40° C at a pressure of 80 cm (water column). After 5 hours, the theoretical amount of hydrogen, 135 ml, was consumed and the hydrogenation was halted and the catalyst filtered off. Following, the solution was dried under reduced pressure on a rotary evaporator and the residue comprising 1.6 grams was crystallized from a 1:5 acetone-hexane mixture, so yielding D-6-methyl-8-β-isopropylaminoethylergolin-I, m.p. 105°-107° C, $[\alpha]_D^{20} -95°$ (c = 0.5, pyridine).

Bis-(hydrogen maleate) of this compound was prepared by adding 0.232 gram of maleic acid in 1 ml. of methanol to a solution comprising 0.31 gram of the ergolin-I compound in 2 ml of methanol. The salt precipitated and was filtered and crystallized from ethanol, yielding 0.45 gram of the salt, m.p. 166°-167° C (decomposition; $[\alpha]_D^{20} -38.5°$ (c = 0.5, water).

EXAMPLE 2

D-6-methyl-8-β-dimethylaminoethylergolin-I 0.22 ml (3 mmol) of a 44% aqueous solution of formaldehyde, and 0.3 ml of an aqueous Raney nickel suspension were added to a solution comprising 0.27 gram (1 mmol) of D-6-methyl-8-β-aminoethylergolin-I in 15 ml of methanol. The resultant mixture was hydrogenated in a rocking autoclave for 2 hours at a temperature within the range of 40°-50° C under 60 atmospheres of hydrogen. After cooling, the catalyst was filtered off and the filtrate dried under reduced pressure. The residue was crystallized from acetone, so yielding colorless platelets of D-6-methyl-8-$\beta$-dimethylaminoethylergolin-I, m.p. 200°-202° C (decomposition); $[\alpha]_D^{20}$ −97.5° (c = 0.5 pyridine).

EXAMPLE 3

D-6-methyl-8-$\beta$-propylaminoethylergolin-I bis (hydrogen maleate)

0.064 gram (1.1 mmol) of propionaldehyde and 15 mg of Adams catalyst were added to a solution comprising 0.27 gram (1 mmol) of D-6-methyl-8-$\beta$-aminoethylergolin-I in 15 ml of ethanol and the mixture hydrogenated with shaking at a temperature within the range of 30°-40° C at a hydrogen pressure of 20 cm of mercury. Hydrogenation was continued with the theoretical amount of hydrogen was consumed, about 25 ml. The catalyst was then filtered off and the solvent evaporated under diminished pressure. The residue comprising 0.29 gram was dissolved in 2 ml of methanol and a solution comprising 0.22 gram of maleic acid in 1 ml of methanol added thereto. The resultant D-6-methyl-8-$\beta$-propylaminoethylergolin-I-bis-(hydrogen maleate) was crystallized from ethanol in the form of colorless needles, m.p. 104°-106° C; $[\alpha]_D^{20}$ −36.4° (c = 0.5, water).

The foregoing procedure was repeated using corresponding aldehydes or ketones rather than propionaldehyde to yield the following bis-(hydrogen maleates):

a. D-6-methyl-8-$\beta$-ethylaminoethylergolin-I-bis-(hydrogen maleate), m.p. 180°-182° C (ethanol); $[\alpha]_D^{20}$ − 38.5° (c = 0.5, water);

b. D-6-methyl-8-$\beta$-butylaminoethylergolin-I-bis-(hydrogen maleate), m.p. 117°-118° C (ethanol, $[\alpha]_D^{20}$ −37.0° C (c = 0.5, water);

c. D-6-methyl-8-$\beta$-isobutylaminoethylergolin-I-bis-(hydrogen maleate), m.p. 155°-156° C (ethanol, $[\alpha]_D^{20}$ −39.0° C (c = 0.5, water);

d. D-6-methyl-8-$\beta$-(1-methylpropyl)aminoethylergolin-I-bis-(hydrogen maleate), m.p. 147°-148° C (ethanol), $[\alpha]_D^{20}$ −35.0° C (c = 0.5, water);

e. D-6-methyl-8-$\beta$-(1-methylbutyl)amino-ethylergolin-I-bis-(hydrogen maleate), m.p. 140°-141° C (ethanol), $[\alpha]_D^{20}$ −34.0° C (c = 0.5, water);

f. D-6-methyl-8-$\beta$-(1-ethylpropyl)aminoethylergolin-I-bis-(hydrogen maleate), m.p. 183°-184° C (ethanol), $[\alpha]_D^{20}$ −37.0° C (c = 0.5, water); and g. D-6-methyl-8-$\beta$-benzylaminoethylergolin-I-bis-(hydrogen maleate), m.p. 179°-181° C (ethanol), $[\alpha]_D^{20}$ −35.0° C (c = 0.5, water); and h. D-6-methyl-8-$\beta$-(4-methoxybenzyl)aminoethylergolin-I-bis-(hydrogen maleate), m.p. 148°-149° C (ethanol, $[\alpha]_D^{20}$ −42.0° C (c = 0.5, water).

EXAMPLE 4

D-1,6-dimethyl-8-$\beta$-isopropylaminoethylergolin-I-bis-(hydrogen maleate)

The procedure of Example 3 was repeated utilizing 0.28 gram (1 mmol) of D-1,6-dimethyl-8-$\beta$-aminoethylergolin-I and 0.064 gram of acetone. The resultant product was comprised of 0.50 gram of D-1,6-dimethyl-8-$\beta$-isopropylaminoethylergolin-I-bis-(hydrogen maleate), m.p. 193°-195° C (ethanol, $[\alpha]_D^{20}$ −41.0° C (c = 0.5, water).

EXAMPLE 5

D-6-methyl-8-$\beta$-(1-phenylethyl)aminoethylergolin-I-bis-(hydrogen maleate)

0.13 gram of acetophenone and 15 mg of Adams catalyst were added to a solution comprising 0.27 gram (1 mmol) of D-6-methyl-8-$\beta$-aminoethylergolin-I in 10 ml of ethanol and the mixture hydrogenated in a rocking autoclave for 15 hours at a temperature within the range of 115°-120° C and 70 atmospheres of hydrogen. After cooling of the reaction mixture, the catalyst was filtered off, the solvent evaporated under reduced pressure and the residue purified by chromatography on a silica gel column using a 9:1 chloroformethanol eluant mixture. Fractions containing the desired compound were combined, the solvent evaporated and the corresponding bis(hydrogen maleate) formed by reaction with maleic acid in ethanol. Recrystallization of the product from ethanol yielded colorless needles of D-6-methyl-8-$\beta$-(1-phenylethyl)aminoethylergolin-I-bis-(hydrogen maleate), m.p. 126°-128° C, $[\alpha]_d^{20}$ −35.0° C (c = 0.5, water).

The procedure described above was repeated using p-methoxyacetophenone rather than acetophenone, so yielding D-6-methyl-8-$\beta$-(1-p-methoxyphenylethyl)-aminoethylergolin-I-bis-(hydrogen maleate), m.p. 155°-157° C (ethanol), $[\alpha]_D^{20}$ −36.0° C (c = 0.5, water).

EXAMPLE 6

D-6-methyl-8-$\beta$-ethylaminoethylergolin-I-bis-(hydrogen maleate)

A solution comprising 0.31 gram (1 mmol) of D-6-methyl-8-$\beta$-acetylaminoethylergolin-I in 30 ml of tetrahydrofuran was added dropwise under nitrogen to a stirred suspension comprising 0.2 gram ($\simeq$ 5 mmol) of lithium aluminum hydride in tetrahydrofuran (25 ml) at room temperature. The reaction mixture was refluxed for 2 hours and yielded a white precipitate which was cooled with ice and decomposed by dropwise addition of 10 ml of 95% aqueous ethanol. The insoluble inorganic residue was filteres, washed with an 8:2 chloroformethanol mixture and the combined filtrates dried. The resultant product comprising 0.3 gram was converted into the corresponding bis-hydrogen maleate which on crystallization from ethanol melts at 180°-182° C; $[\alpha]_D^{20}$ −38.5° C (c = 0.5, water).

EXAMPLE 7

D-6-methyl-8-$\beta$-dimethylaminoethylergolin-I

The desired compound was obtained using the molar ratios and the procedure of Example 6 and using D-6-methyl-8-ergolinyl-I-acetic acid dimethylamide rather than the noted ergolin-I starting compound. The product comprising 0.3 gram was purified by crystallization from acetone and evidenced a melting point within the range of 200°-202° C (decomposition); $[\alpha]_D^{20}$ −97.5° C (c = 0.5, pyridine).

As indicated hereinabove, compounds of formula (1) reduce the weight of prostate in test animals, namely, rats. Additionally, such compounds (e.g., D-6-methyl-8-$\beta$-isopropylaminoethylergolin-I) administered orally in the form of an aqueous solution of the bis(hydrogen maleate) in mice evidences acute $LD_{50}$ = 130 mg of base/kg. The melting points set forth above were determined on a Kofler block and are in degrees Centigrade. The specific rotation values relate to compounds free of crystal solvent.

What is claimed is:

1. D-6-methyl-8-$\beta$-isopropylaminoethylergolin-I.

* * * * *